US011291992B2

(12) United States Patent
Dutry et al.

(10) Patent No.: US 11,291,992 B2
(45) Date of Patent: Apr. 5, 2022

(54) ON-SITE DIAGNOSTIC SYSTEM AND THE METHOD THEREOF

(71) Applicant: SANWA BIOTECH LTD, Hong Kong (CN)

(72) Inventors: Isabelle Cécile Angèle Dutry, Hong Kong (CN); Kin Sun Ip, Hong Kong (CN); Kelvin Chiu, Hong Kong (CN); Wai Lam William Yim, Hong Kong (CN); Yiu Ting Richard Lau, Hong Kong (CN)

(73) Assignee: Sanwa BioTech Ltd, Hong Kong (HK)

( * ) Notice: Subject to any disclaimer, the term of this patent is extended or adjusted under 35 U.S.C. 154(b) by 695 days.

(21) Appl. No.: 15/328,886

(22) PCT Filed: Aug. 5, 2015

(86) PCT No.: PCT/CN2015/000567
§ 371 (c)(1),
(2) Date: Jan. 24, 2017

(87) PCT Pub. No.: WO2016/019701
PCT Pub. Date: Feb. 11, 2016

(65) Prior Publication Data
US 2017/0209862 A1 Jul. 27, 2017

Related U.S. Application Data

(60) Provisional application No. 62/033,116, filed on Aug. 5, 2014.

(51) Int. Cl.
*B01L 3/00* (2006.01)
*G01N 33/543* (2006.01)
(Continued)

(52) U.S. Cl.
CPC .... *B01L 3/502715* (2013.01); *G01N 21/6428* (2013.01); *G01N 21/77* (2013.01);
(Continued)

(58) Field of Classification Search
CPC .......... B01L 3/502715; B01L 3/50273; B01L 2200/0684; B01L 2300/069;
(Continued)

(56) References Cited

U.S. PATENT DOCUMENTS 7,648,619 B2 1/2010 Chuang et al.
2003/0196900 A1 10/2003 Chen et al.
(Continued)

FOREIGN PATENT DOCUMENTS

CN 103403547 A 11/2013
DE 102010061909 5/2012
(Continued)

*Primary Examiner* — Samuel P Siefke
(74) *Attorney, Agent, or Firm* — Owens Law Firm, PC

(57) ABSTRACT

A portable and completely self-contained apparatus(20) for detecting analyte and the methods of use thereof is described. The apparatus (20) includes a microfluidic cartridge driver unit (30), an optical inspection unit (32), and a control unit (28) and a power supply unit, which can run the binding and detection of the analyte without any fluidic interfaces to the instrument. The microfluidic cartridge driver unit (30) receives microfluidic cartridge (22) that holds a microarray and integrated microfluidic chip (24) for delivering the analyte to perform different process steps in the detection of analyte. A complete detection of analyte using the invention takes only a few minutes.

10 Claims, 12 Drawing Sheets

(51) Int. Cl.
*G01N 21/77* (2006.01)
*G01N 21/84* (2006.01)
*G01N 21/64* (2006.01)

(52) U.S. Cl.
CPC ... *G01N 21/8483* (2013.01); *G01N 33/54366* (2013.01); *B01L 3/50273* (2013.01); *B01L 2200/0684* (2013.01); *B01L 2300/069* (2013.01); *B01L 2300/0654* (2013.01); *B01L 2300/0887* (2013.01); *B01L 2300/16* (2013.01); *B01L 2400/0493* (2013.01); *G01N 2021/7786* (2013.01); *G01N 2201/0245* (2013.01); *G01N 2201/0612* (2013.01); *G01N 2333/11* (2013.01)

(58) Field of Classification Search
CPC ......... B01L 2300/16; B01L 2400/0493; B01L 2300/0887; B01L 2300/0654; G01N 21/6428; G01N 21/8483; G01N 21/77; G01N 33/54366; G01N 2333/11; G01N 2201/0612; G01N 2201/0245; G01N 2021/7786

See application file for complete search history.

(56) References Cited

U.S. PATENT DOCUMENTS

| | | |
|---|---|---|
| 2004/0257906 A1 | 12/2004 | Scriba et al. |
| 2006/0257991 A1 | 11/2006 | McDevitt et al. |
| 2007/0166770 A1* | 7/2007 | Hsieh ............... G01N 1/30 435/7.2 |
| 2011/0201099 A1* | 8/2011 | Anderson ............ G01N 21/05 435/287.2 |
| 2012/0177543 A1 | 7/2012 | Battrell et al. |
| 2013/0029867 A1 | 1/2013 | Tanaami et al. |
| 2013/0255812 A1 | 10/2013 | Otto et al. |
| 2013/0337576 A1 | 12/2013 | Zhu et al. |

FOREIGN PATENT DOCUMENTS

| | | |
|---|---|---|
| DE | 102010061910 | 5/2012 |
| EP | 2559489 | 2/2013 |
| JP | 2007-178428 | 7/2007 |
| JP | 2009-525728 | 7/2009 |
| JP | 2010-503516 | 2/2010 |
| JP | 2012-095583 | 5/2012 |
| JP | 2013-024818 | 2/2013 |
| WO | 2006066541 A1 | 6/2006 |
| WO | 2007112114 | 10/2007 |
| WO | 2010088514 | 8/2010 |
| WO | 2013112755 | 8/2013 |
| WO | 2013124448 A1 | 8/2013 |
| WO | 2014085926 | 6/2014 |
| WO | 2011/071772 A2 | 6/2016 |

* cited by examiner

ON-SITE DIAGNOSTIC SYSTEM AND THE METHOD THEREOF

CROSS-REFERENCE TO RELATED APPLICATION

This application claims benefit under 35 U.S.C. § 119(e) of U.S. Provisional Application having Ser. No. 62/033,116 filed 5 Aug. 2014, which is hereby incorporated by reference herein in its entirety.

FIELD OF INVENTION

This invention relates to an apparatus for detecting analyte and the method of use thereof.

BACKGROUND OF INVENTION

Traditional apparatus for detecting analyte in a sample (e.g. pathogen present in the blood serum, body fluid, nasal/nasopharyngeal swabs or saliva of a target individual) for e.g. diagnostic purposes involves relatively large amount or volume of sample or analyte. The sample has to be transported to a well-equipped laboratory with bulky instruments and may require several steps of processes, such as sample preparation, bioassay test or optical inspection. In other words, many traditional apparatus for detecting analyte are expensive and time consuming.

SUMMARY OF INVENTION

In the light of the foregoing background, it is an object of the present invention to provide an improved apparatus for detecting one or more analyte(s).

Accordingly, the invention, in one aspect, is an apparatus for detecting at least one or more analyte(s) from a sample including (a) a microfluidic cartridge driver unit including a cartridge chamber configured to receive a microfluidic cartridge having a first portion for interacting or reacting with the analyte; and at least one electrical connector configured to connect with the microfluidic cartridge for electrical connection there with; (b) an optical inspection unit configured to detect at least one signal generated from the first portion due to the presence of the analyte at a predetermined condition, the unit including a collecting tray configured to receive at least the first portion of the microfluidic cartridge; an illumination system configured to deliver light directly to the first portion, there by providing the predetermined condition;and an optical sensor configured to detect the signal; and (c) a control unit configured to control the quantitative and qualitative analysis, interfacing, and storage of signal obtained from the optical inspection unit, and to control and monitor the operation of the apparatus.

In another aspect, the present invention is a microfluidic cartridge including (1) a microfluidic chip including a plurality of reservoirs, wherein at least one of the reservoirs is configured to receive a sample which may include an analyte and the remaining reservoir is configured to hold at least one reagent; and (2) a diagnostic chip detachably attached to the microfluidic chip, wherein the microfluidic chip is further configured to drive the sample and the reagent from the plurality of reservoirs to the diagnostic chip; and wherein the diagnostic chip is pre-coated with an array of detection spots, which is configured to interact or react with the analyte for generating at least one signal at a predetermined condition. According to another aspect, the present invention is a method for detecting at least one analyte including the steps of (a) loading appropriate amount of at least one reagent and at least one sample including the analyte(s), onto a microfluidic cartridge; (b)docking the microfluidic cartridge to a cartridge chamber configured to receive the microfluidic cartridge; (c) directing the flow of the reagent and the sample to a first portion of the microfluidic cartridge through at least one microfluidic channel of the microfluidic cartridge in a predetermined sequence upon receiving electrical current from the cartridge chamber via at least one electrical connection; (d) providing a predetermined condition to the first portion of the microfluidic cartridge to generate at least one signal; (e) detecting at least one signal and collecting data using an optical sensor; and (f) analyzing the data with a microprocessor to determine the presence of the analyte quantitatively or qualitatively, wherein the first portion of the microfluidic cartridge is pre-coated with an array of detection spots, which is configured to interact or react with the analyte for generating at least one signal at the predetermined condition.

There are many advantages to the present invention. The apparatus for detecting analyte of the present invention involves relatively small amount or volume of sample (e.g. from a few microliters (µl) to hundreds of µl) while using an integrated reaction-to-detection instrument/methodology. As such, this is a genuine "field testing equipment" that will provide true convenience to field personnel. As a result, special handling and transportation of analyte to the laboratory and the excessive transportation time that may affect the quality of analyte are greatly reduced.

Another advantage of the present invention is that the apparatus of the invention requires little or no sample preparation compared to conventional diagnostic method or system, thereby reducing processing time.

Another advantage of the invention is that it can be applied in various area of diagnosis and food safety analysis. Such application includes, but not limited to animal immunodiagnostics (e.g. Swine Influenza virus (e.g. H1N1) infection, Porcine Reproductive and Respiratory Syndrome (PRRS), Bovine Foot-and-Mouth Disease (FMD), Classical Swine Fever (CSFV) infection, and Bovine Spongiform Encephalopathy (BSE) Infectious Disease), food safety test (e.g. detection of food allergens (e.g. peanuts, seafood), aflatoxin and melamine), the clinical detection for human subjects (e.g. the detection of infectious diseases (e.g. sexually transmitted diseases (STD), Ebola virus, Middle East respiratory syndrome corona virus (MERS-CoV) and Influenza virus infection), tropical diseases (e.g. Dengue virus and Japanese Encephalitis virus infection) and new emergent infectious diseases which fall within antigen/antibody immunological mechanism in their pathological pathway). Some of the preferred implementations can be adapted to analyze for multiple analytes within the same sample and same process, significantly reducing the cost and processing time involved for the checking for multiple diseases/analytes.

As a summary, the advantages of the apparatus of the instant invention for detecting analyte are low cost, time-and-space saving, portable and require low degree of skills and technicians to conduct a complete analyte detection rapidly at scale and on site efficiently.

BRIEF DESCRIPTION OF FIGURES

A more complete understanding of the present invention can be achieved by reference to the following detailed description when in conjunction with the accompanying drawing wherein.

DETAILED DESCRIPTION OF THE PREFERRED EMBODIMENTS

As used herein and in the claims, "comprising" means including the following elements but not excluding others.

"Analyte" includes, but not limited to, pathogens and biomolecules present in e.g. body fluids or blood serum sample from a target individual, including, but not limited to, e.g. animal or human subjects.

Figure 1:
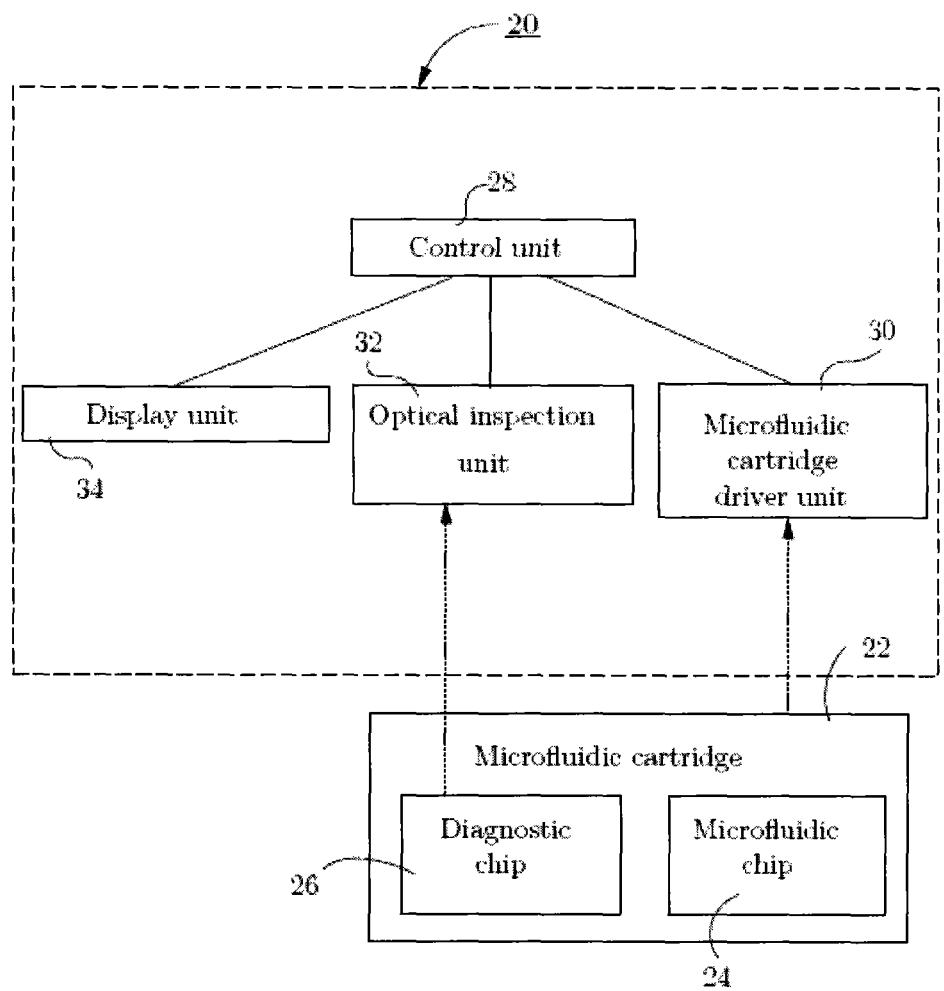
FIG. 1 is a block diagram illustrating a diagnostic system, according to an embodiment of the present invention.
Figure 2:
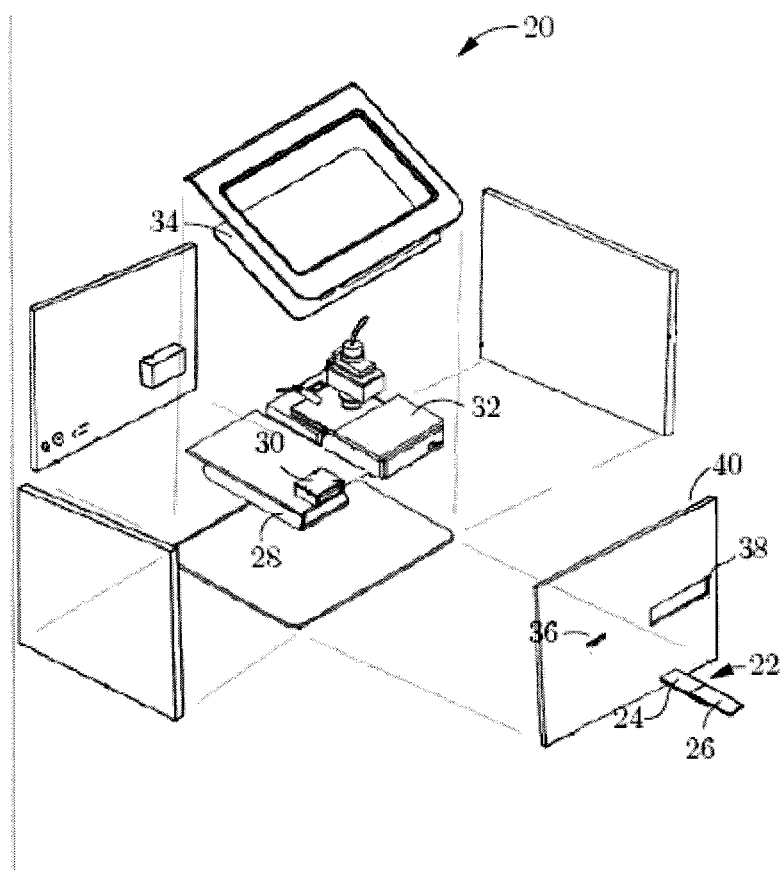
FIG. 2 is a schematic view of the diagnostic system, according to the same embodiment of the present invention.

FIG. 1 and FIG. 2 show an on-site and fast result generating diagnostic system including a diagnostic apparatus 20 and a microfluidic cartridge 22, which operates with the diagnostic apparatus 20. The microfluidic cartridge 22 which includes a microfluidic chip 24 and a diagnostic chip 26 is configured to collect and manipulate at least one sample, which may include at least one analyte. The microfluidic cartridge 22 also receives or holds at least one reagent. The diagnostic apparatus 20, which is a portable, hand carriable and compact device, includes a control unit 28, a microfluidic cartridge driver unit 30, an optical inspection unit 32 and a display unit 34. The control unit 28 controls and is connected to the microfluidic cartridge driver unit 30, the optical inspection unit 32 and the display unit 34. The microfluidic cartridge driver unit 30 is configured to receive and drive the microfluidic cartridge 22 such that the sample collected and the reagent run through the microfluidic chip 24 and the diagnostic chip 26 in a predetermined sequence. The optical inspection unit 32 is configured to receive and inspect the diagnostic chip 26 for analyzing the presence of analyte. The display unit 34 is configured to display relevant information including analyzed/diagnostic results to users. FIG. 2 shows that the control unit 28, microfluidic cartridge driver unit 30, optical inspection unit 32 and display unit 34 are enclosed in a self-contained diagnostic apparatus including a microfluidic cartridge receiving hole 36 and a diagnostic chip receiving hole 38 on its front panel 40 for receiving the microfluidic cartridge 22 and the diagnostic chip 26 respectively.

Figure 3:
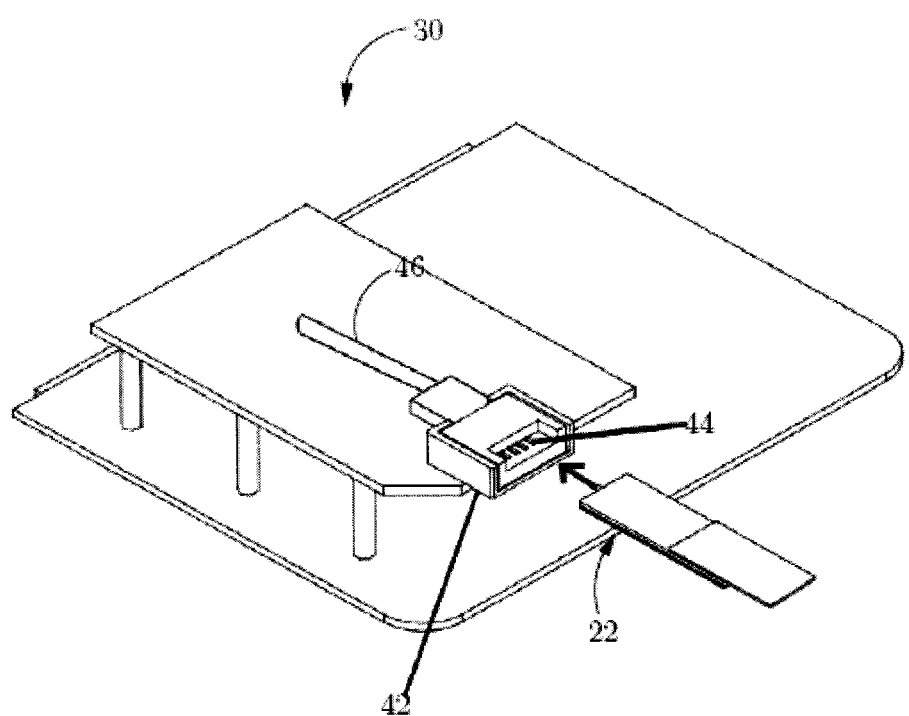
FIG. 3 is a schematic view of a microfluidic cartridge driver unit of the diagnostic system, according to the same embodiment of the present invention.

The microfluidic cartridge driver unit 30 as shown in FIG. 3 comprises a cartridge chamber 42 for receiving the microfluidic cartridge 22. The cartridge chamber 42 includes electrical connectors 44 that act as an interface for the microfluidic cartridge 22 to drive/control and provide power/electrical current to the microfluidic cartridge 22 to perform predetermined sequences for driving the reagent and sample from the microfluidic chip 24 to the diagnostic chip 26 for reaction. The predetermined sequences will be discussed in detail below. Control signals and power are provided to the electrical connectors 44 though a connection cable 46.

Figure 4:
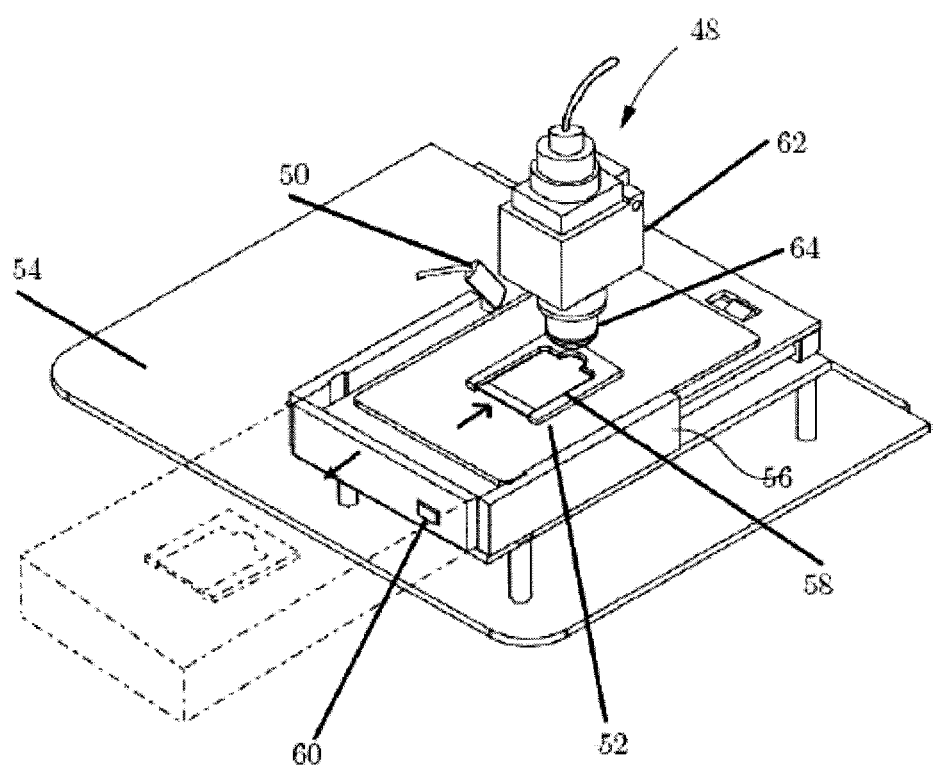
FIG. 4 is a schematic view of an optical inspection unit of the diagnostic system, according to the same embodiment of the present invention.

The optical inspection unit 32 as shown in FIG. 4 is a compact size that weighs less than a few kilograms (kg) for on-site analyte analysis/detection. The optical inspection unit 32 includes an optical sensor 48, illumination system 50 and diagnostic chip collecting tray 52, which is supported by a supporting panel 54. The diagnostic chip collecting tray 52 which can be released from a diagnostic chip collecting tray bay 56 includes a diagnostic chip holder 58 and a tray button 60. The tray button 60 activates the release of the diagnostic chip collecting tray 52. At stand-by state, the diagnostic chip collecting tray 52 stays inside the diagnostic chip collecting tray bay 56 (e.g. at the docked position). At this state, the diagnostic chip collecting tray 52 is locked at the diagnostic chip collecting tray bay 56 by a hook while diagnostic chip collecting tray 52 is loaded with a spring. When the tray button 60 is pressed, the diagnostic chip collecting tray 52 is unhooked such that the diagnostic chip collecting tray 52 at the docked position is pushed away from the diagnostic chip collecting tray bay 56 by the spring. As such, the diagnostic chip holder 58 is carried out of the diagnostic apparatus 20 to receive a diagnostic chip 26 of the microfluidic cartridge 22. The diagnostic chip holder 58 is retracted into the diagnostic chip collecting tray bay 56 to the docked position when it is pushed toward the diagnostic apparatus 20.

The illumination system 50 comprises a diode laser radiating at least one laser beam with at least one predetermined wavelength on the diagnostic chip 26 to generate at least one signal. The predetermined wavelength of the laser beam is selected such that at least one signal which is detectableby the optical sensor 48 can be generated. The intensity and the wavelength of the laser beam can be selected/controlled by the user through the control unit 28 for detecting a particular analyte. The laser beam is steered to the diagnostic chip 26 at an angle so as to avoid reflections and to generate the signal at higher quality. The predetermined wavelength, for example, is in a range of 465 to 500 nm, 400 to 700 nm, 430 to 465 nm, 500 to 550 nm, 550 to 580 nm, 580 to 620 nm, or 620 to 700 nm.

The diagnostic chip holder 58 is located beneath the optical sensor 48 and the illumination system 50 when the diagnostic chip collecting tray 52 at its docked position. The optical sensor 48 includes a camera 62 and at least one objective 64 to receive signals from the diagnostic chip 26 generated by radiating a laser light on the diagnostic chip 26 held on the diagnostic chip holder 58 by the illumination system 50. The received signals are then sent to the control unit 28 for analysis. The control unit 28 generally includes microprocessor (CPU), memory, and input/output (I/O) interfaces. The control unit 28 controls the quantitative and qualitative analysis, interfacing, and storage of signal obtained from the optical inspection unit 32, and to control and monitor all the operations of the diagnostic apparatus 20.

Figure 5:
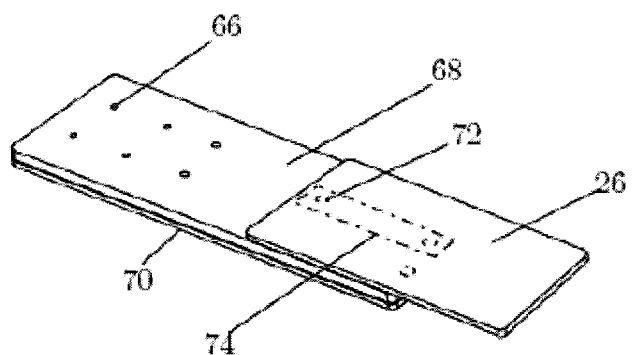
FIG. 5 is a schematic top view of a microfluidic cartridge, according to the same embodiment of the present invention.
Figure 6:
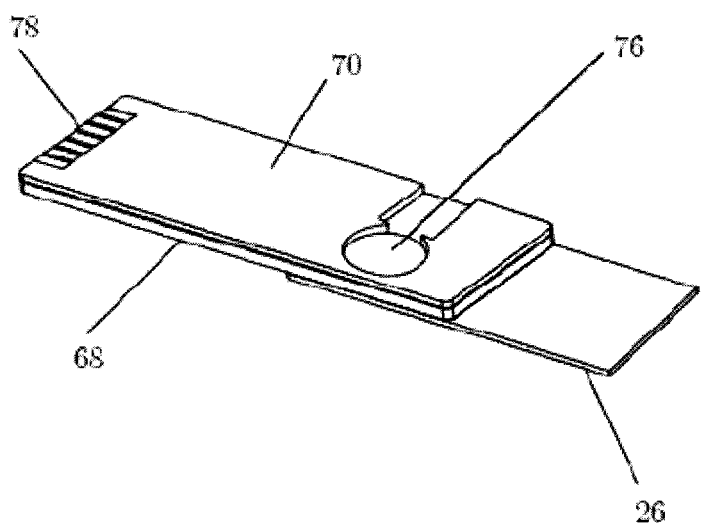
FIG. 6 is a schematic bottom view of a microfluidic cartridge, according to the same embodiment of the present invention.

The microfluidic cartridge 22 as shown in FIG. 5 and FIG. 6 includes the diagnostic chip 26 attached to the microfluidic chip 24. In the implementation shown, it has a dimension smaller than a credit card with a thickness of 1-10 mm. The microfluidic chip 24 includes an electrical connecting interface 78 for receiving control signals and power provided through electrical connectors 44 of the cartridge chamber 42, a top part 68 and a bottom part 70 attached to the top part 68. In this example, the top part 68 and bottom part 70 are assembled together with adhesive materials or by welding process. The bottom part 70 may be made of electrical insulated material such as plastic and resin material. As shown in FIG. 5, the top part 68 has a plurality of micro grooves 66, a channel opening 72 having a fluid connection with the microfluidic chip 24 and an adhesive 74 for attaching the microfluidic chip 24 at the channel opening 72. The bottom 200 part 70 of the microfluidic cartridge has a groove for a microporous membrane 76 to be placed therein as shown in FIG. 6.

Figure 7:
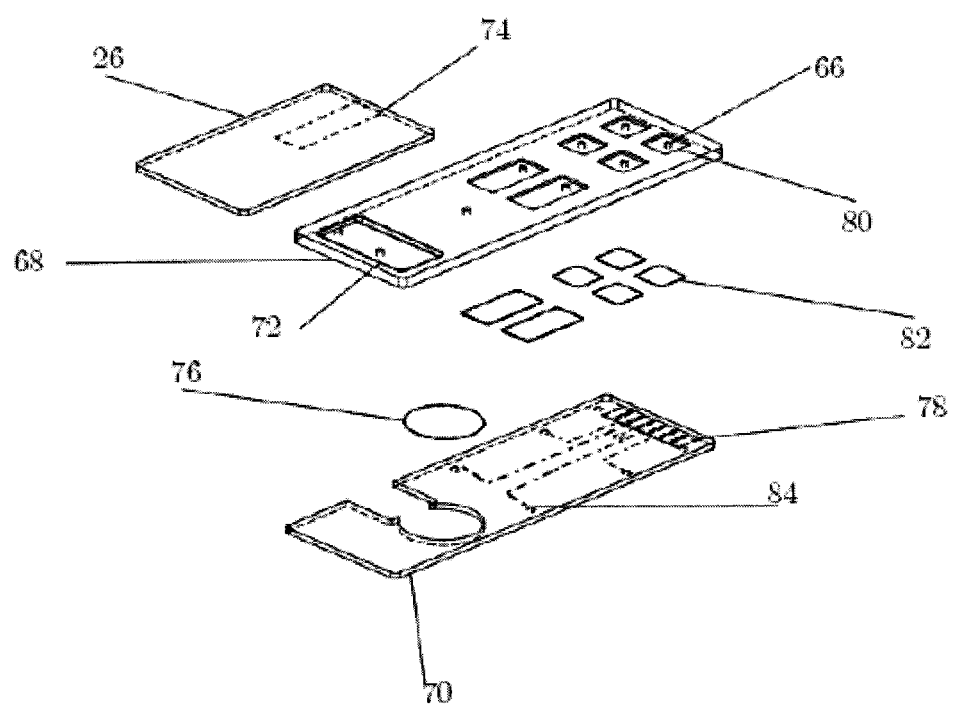
FIG. 7 is a schematic exploded view of a microfluidic cartridge, according to the same embodiment of the present invention.
Figure 8:
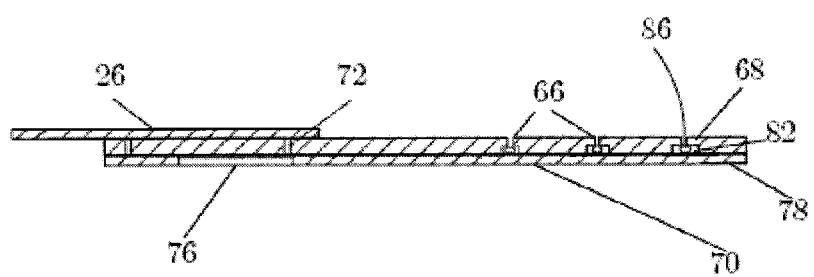
FIG. 8 is a schematic side view of a microfluidic cartridge, according to the same embodiment of the present invention.

Now refers to FIG. 7 and FIG. 8, the top part 68 can be made of acrylic, polycarbonate or similar kind of plastic materials. It may be transparent as to allow the user to observe the status of fluid inside the microfluidic chip 24. The plastic 205 parts can be manufactured by plastic injection process associated with other process such as hot embossing and micro machining method. The top part 68 includes a plurality of micro grooves 66 in a corresponding plurality of reservoirs 80, wherein at least one reservoir is configured to receive the sample from the top and at least one reservoir is configured to hold at least one reagent for facilitating the reaction or interaction between the analyte interacting molecules and analyte. As such, the detection of analyte can be facilitated. The reagent held in the at least one reservoir is selected from the group consisting of washing buffer and blocking buffer. In one embodiment, the washing buffer is Phosphate-buffered saline (PBS) and the blocking buffer is PBS and Bovine serum albumin (BSA). The sample is driven from the microfluidic chip 24 to the diagnostic chip 26 for analyte reaction/interaction on the diagnostic chip 26. In each of the reservoir 80, at least one micro fluidic channel 86 is located beneath the micro grooves 66 at the interface between the top part 68 and bottom part 70 as shown in FIG. 8. The reagent and the sample are driven from the microfluidic chip 24 to the diagnostic chip 26 through the micro fluidic channel 86 and then to channel opening 72. Each of the reservoir 80 is integrated with a micro-pump which is constructed with small amount of hydro gel 82 placed therein. The hydro gels 82 are in contact with electrical conductive circuit traces 84 incorporated onto the built material of the bottom part 70. These micro-pumps are operated by electrical current, which are supplied through electrical conductive circuit traces 84. These micro-pumps push the sample and reagent through the micro fluidic channels 86 whereby the sample is mixed with the reagent to the channel opening 72 by expanding and contracting the hydro gels 82. The expending and contracting of the hydro gels 82 are controlled by the microfluidic cartridge driver unit 30 of the diagnostic apparatus 20 by sending signals and power through the connection between electric connector 44 and the electric connecting interface 78, which is also in electrical connection with the electrical conductive circuit traces 84. The pumps are encapsulated so that it can avoid contamination and cross-contamination issues. The volume of each reservoir 80 is in a range of 1-80 μl.

The diagnostic chip 26 can be made of glass, silicon or plastic and is detachably attached to the microfluidic chip 24 by the adhesive 74. The bottom surface (i.e. the surface facing the channel opening 72) of the diagnostic chip 26, which is pre-coated with an array of detection spots that can react/interact with the analyte present in a sample to generate at least one signal under certain condition (e.g. generating fluorescent signal(s) when radiated by a laser light at certain wavelength), is disposed toward and in fluid communication with the channel opening 72. In one embodiment, the detection spots each include at least one analyte interacting molecule that reacts/interacts with at least one analyte. In one specific embodiment, the analyte interacting molecule is a particular protein or peptide that binds with at least one particular virus/bacteria that is in its intact state or in portion suitable for being detected (e.g. an antigen). The array of detection spots is located within 1-15 millimeter (mm) around the channel opening 72 such that the mixed sample and reagent can spread through the array when it is pumped out of the channel opening 72. The bottom surface of the diagnostic chip 26 facing towards the microfluidic chip 24 is first coated with a first coating for immobilizing the later coated detection spots without modifying the configuration of the detection spots (e.g. keeping the binding sites of the analyte interacting molecule included in the detection spots to be analyte(s) accessible). The first coating should also create a hydrophilic environment for the reaction/interaction of analyte to take place. It is optimized to minimize nonspecific reaction/interaction thus reduce background noise signal in the instant apparatus. Once the first coating is done, detection spots are deposited on the bottom surface of the diagnostic chip 26 in a pre-defined pattern (e.g. an array). A drop-on-demand method is chosen to disperse them onto the diagnostic chip 26. In one embodiment, the drop-on-demand method can be performed by a microarray printer. The diagnostic chip 26 with the mixed reagent and sample (which may include the analyte) reacted/interacted there on can be detached from the microfluidic chip 24 and be placed to the diagnostic chip holder 58 for further analysis by the optical inspection unit 32. The mixed sample and reagent on the diagnostic chip 26 may be dried before or after the diagnostic chip 26 being detached from the microfluidic chip 24.

Figure 9:
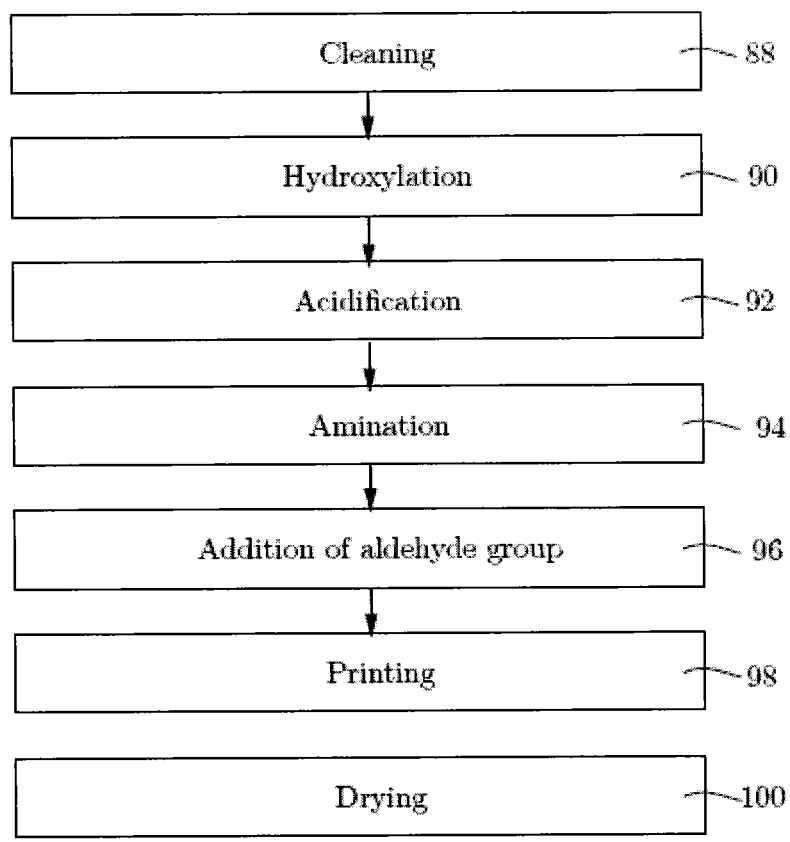
FIG. 9 is a flow chart of coating process and the deposition of detection spots on the diagnostic chip, according to one embodiment of the present invention.
Figure 10:
FIG. 10 depicts the detection of fluorescent-tagged H7N9 antigen.
Figure 11:
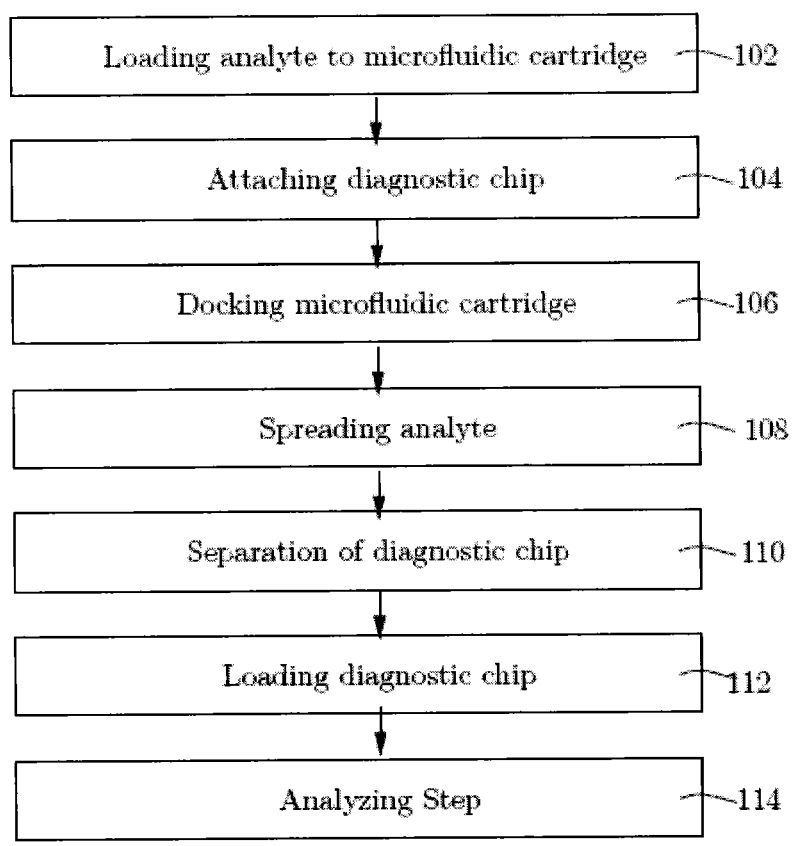
FIG. 11 is a flow chart of the on-site diagnostic method and an operation of the diagnostic system, according to one embodiment of the present invention.

In one exemplary embodiment, the steps of coating process and the deposition of detection spots containing e.g. antigen of the H7N9 influenza virus on the surface of the diagnostic chip 26 are shown in FIG. 9 and are detailed below:

For the cleaning step 88: The diagnostic chip 26 of glass material is partly immersed in a 250 milliliter (ml) beaker containing acetone. Ultra-sonication is then performed for 5 minutes (mins) so as to clean the immersed part of the diagnostic chip 26. Diagnostic chip 26 is then transferred with forceps to another 250 ml beaker containing ethanol. Ultra-sonication is then performed again for 5 mins.

For the hydroxylation step 90: Seventy-five (75) ml of 95% sulfuric acid is transferred into a 250 ml beaker. Twenty-five (25) ml of 34.5% volume to volume (v/v) hydrogen peroxide is then pipetted to the same beaker, so that the final concentration of hydrogen peroxide is 8.63%, and that the resultant ratio between the volume of the concentrated sulfuric acid and the 34.5% hydrogen peroxide (piranha solution) is 1:3 v/v. Consequently, the diagnostic chip 26 from the cleaning step 88 is then partly immersed in above solution at room temperature for 2 hours (hrs). The treated diagnostic chip 26 is then picked up from the Piranha solution with forceps and is rinsed with ultrapure water using a wash bottle for 5 mins. The piranha solution is discarded into a waste bottle. Next, the treated diagnostic chip 26 is transferred with forceps to a 250 ml beaker containing 95% absolute ethanol. Ultra-sonication is then performed for 5 mins. Such step for the treated diagnostic chip 26 is then repeated in another 250 ml beaker containing purified water for one more time.

For the acidification step 92: Twenty-five (25) ml of hydrochloric acid is transferred to a 50 ml reaction tube. Twenty-five (25) ml of ethanol is then added to the same tube. The diagnostic chip 26 from the hydroxylation step 90 is then transferred with forceps to the above solution and is reacted at 37 degree Celsius (° C.) for 3 hrs. The treated diagnostic chip 26 is then picked up from the solution with forceps and is rinsed with ultrapure water using a wash bottle for 5 mins. The solution is discarded into a waste bottle. Consequently, the washed diagnostic chip 26 is then transferred with forceps to a 250 ml beaker containing 95% absolute ethanol. Ultra-sonication is then performed for 5 mins.

The diagnostic chip 26 is then transferred with forceps to another 250 ml beaker containing purified water. Ultra-sonication is then performed again for 5 mins. After that, the treated diagnostic chip 26 is then transferred with forceps to a 250 ml beaker and is incubated in an oven for drying at 60° C. for 30 mins, before proceeding to the amination step 94 as described below.

For the amination step 94: Six point six hundred and forty one (6.641) gram (g) of (3-Aminopropyl) triethoxysilane (APTES) (moisture sensitive) at room temperature is pipetted to a 50 ml reaction tube (first use). Forty-three (43) ml of ethanol is then pipetted to the same tube. Next, 0.1 ml of acetic acid is then added to the same tube. The treated diagnostic chip 26 from acidification step 92 is then transferred with forceps to the above solution is reacted at 50° C. for 24 hrs. Consequently, the diagnostic chip 26 is then transferred with forceps to a 250 ml beaker containing 95% absolute ethanol. Ultra-sonication is then performed for 5 mins. The diagnostic chip 26 is then transferred with forceps to another 250 ml beaker containing purified water, and ultrasonication is then performed again for 5 mins. After that, the treated diagnostic chip 26 is then transferred with forceps to a 250 ml beaker and is incubated in an oven for drying at 120° C. for 30 mins.

For the addition step 96—adding aldehyde group: twenty-five percent glutaraldehyde is prepared each in 50 ml reaction tube. The treated diagnostic chip 26 from the amination step 94 is then transferred with forceps to the above solution and is reacted at room temperature for 24 hrs. Consequently, the diagnostic chip 26 is then transferred with forceps to a 250 ml beaker containing 95% absolute ethanol. Ultra-sonication is then performed for 5 mins The diagnostic chip 26 is then transferred with forceps to another 250 ml beaker containing purified water and ultra-sonication is then performed again for 5 mins. Such step is then repeated in another 250 ml beaker containing purified water for one more time. Next, the treated diagnostic chip 26 is then transferred with forceps to a 250 ml beaker and is incubated in an oven for drying at 60° C. for 30 mins.

In an alternative embodiment, the diagnostic chip 26 is rinsed with deionized water, and is then ultra-sonicated for 5 mins in a 1:3 volume to volume (v/v) cleaning detergent: deionized water mixture. The cleaned diagnostic chip 26 is subsequently immersed for 5 mins in deionized water (after decantation), and is finally immersed for 5 mins in acetone. The cleaned diagnostic chip 26 is then dried with compressed air. Next, 3-glycidoxypropyltrimethoxysilaneis then dissolved in acetone and is mixed with collodion solution (10%, obtained from Wako) with a pipette. The diagnostic chip 26 is dipped into this mixture and is withdrawn from the mixture slowly. The diagnostic chip 26 is then dried in air and turned to a white film. The coated diagnostic chip 26 is further incubated at 80° C. for 1 hour. The diagnostic chip 26 will then be submerged in 20 ml of ethanol for 5 mins after the equilibration at room temperature. The diagnostic chip 26 is then rinsed thoroughly with water, and is subsequently rinsed with acetone and water. The diagnostic chip 26 turned transparent and could be stored at room temperature before use for e.g. the printing step 98 as described below.

For the printing step 98—printing of PBS buffer, H7N9 antigen or BSA on the diagnostic chip 26 coated with aldehyde group as described in step 96, or on the transparent diagnostic chip 26 obtained from the acidification step 92: For printing with PBS buffer, prepare ink preparation of 40% glycerol in 4 ml PBS and fill the same in a printer cartridge. For printing H7N9 antigen, prepare ink preparation of 0.1 ml H7N9 antigen (from Sino Biological, at 1 milligram (mg)/ml) and 40% glycerol in 1.5 ml PBS, and fill the mixture in a printer cartridge. For printing with BSA, prepare ink preparation with 1 ml of 1000 microgram (μg)/ml of BSA (from Thermo, Product number 23208) solution with 40% glycerol in 4 ml PBS, and fill the mixture in a printer cartridge. Next, the FUJIFILM Dimatrix Materials Printer (model number DMP-2831) is set up. The prepared cartridge is then fixed onto the print head (precaution: ensure that no air bubbles are observed in the solution especially those being trapped in the inlet flow channel. If not, finger-tap on the cartridge until the bubbles are removed from the channel). The solution drop dripping stability from the 16 nozzles is then verified. At least one nozzle with good conditions is also chosen for the dot printing onto the treated diagnostic chip 26 from the addition step 96. The H7N9 antigen or BSA dot in 200 μm is then printed on the treated diagnostic chip 26. The printed diagnostic chip 26 is then transferred in a petri dish with cover, and is then incubated in drying oven at 37° C. for 2 hrs in the drying step 100.

The printed side of the processed diagnostic chip 26 in glass material from the drying step 100 is then attached using adhesive 74 to the top part 68 of the microfluidic chip 24 loaded with sample for detection as aforesaid, and can be removed from the microfluidic chip 24 for optical inspection by the optical inspection unit 32 after the reaction/interaction with sample containing analyte. An exemplary print pattern (4× magnified) of the antigen printed on a glass diagnostic chip treated with 25% glutaraldehyde for 24 hrs as revealed by using 1:80 dilution of H7N9 antibody is shown in FIG. 10.

Now turning to anon-site diagnostic method and an operation of the diagnostic system as shown in FIG. 11. The microfluidic chip 24 is first loaded with an appropriate amount of sample (e.g. a blood serum sample) that may contain analyte by dispensing the sample into the reservoirs 80 in a loading step 102. Reagent purposed for facilitating analyte detection is/are also dispensed similarly to separate reservoirs 80. The reagent held in the at least one reservoir is selected from the group consisting of washing buffer and blocking buffer. In one embodiment, the washing buffer is PBS and the blocking buffer is PBS and BSA. Then in the attaching step 104, the diagnostic chip 26 is brought to the adhesive 74 to attach the diagnostic chip 26 to the microfluidic chip 24. The diagnostic chip 26 surface having the array of the detection spots and the first coating should face toward the channel opening 72 and the adhesive 74 at the top part 68 of the microfluidic chip 24. The array of the detection spots and the first coating should be located within the 1-15 mm vicinity of the channel opening 72. The microfluidic cartridge 22 formed by attaching microfluidic chip 24 and diagnostic chip 26 is then 375 docketed to the cartridge chamber 42 of the microfluidic cartridge driver unit 30 in docking step 106 by putting the electric connecting interface 78 through the microfluidic cartridge receiving hole 36, such that the electric connecting interface 78 will be in contact with electrical connectors 44. Then the mixed sample and reagent is spread across the array of detection spots in the spreading analyte step 108. This is done by flowing the sample and reagent from the reservoirs 80 through the microfluidic channels 86 of the microfluidic chip 24 to the channel opening 72. Upon receiving an electrical current and signals by electric connecting interface 78 from the microfluidic cartridge chamber via electrical connectors 44, the micro-pumps drive the sample through themicrofluidic channels 86 at the time, speed and sequences as instructed by the microprocessor of the control unit 28. The mixed sample and reagent (the sample is mixed with the reagent while flowing through the microfluidic channels 86 of the microfluidic chip 24 as aforesaid) that exits the channel opening 72 spreads across the bottom surface of the diagnostic chip 26. Any air bubbles in the reservoir 80 will be removed through the microporous membrane 76 located at the bottom part 70 of the microfluidic chip 24 as the sample passes through it from the microfluidic channels 86. The area where the mixed sample and reagent spread covers the place where the array of detection spots locates such that the analyte can react/interact with the analyte interacting molecule in the detection spots. In one embodiment, step 108 can further include the step of further driving the microfluidic chip 24 to spread a second auxiliary reagent, which is located at one of the reservoirs 80, by flowing through the microfluidic channels 86 of the microfluidic chip 24 to the diagnostic chip 26 for attaching a secondary molecule for facilitating the detection of reacted or interacted analyte after the mixed sample and reagent is spread on the array of detection spots. When pumping and the analyte reaction/interaction are stopped, the microfluidic cartridge 22 is unplugged from the cartridge chamber 42 of the microfluidic cartridge driver unit 30. The diagnostic chip 26 with the analyte thereon is then detached from the microfluidic chip 24 in the separation step 110. The mixed sample and reagent on the diagnostic chip 26 may be dried before or after the diagnostic chip 26 being detached from the microfluidic chip 24. In the diagnostic chip loading step 112, the diagnostic chip collecting tray 52 and the diagnostic chip holder 58 are then released from the diagnostic chip collecting tray bay 56 and is extended out of the diagnostic apparatus 20 for receiving the diagnostic chip 26. The diagnostic chip 26 is placed and is held at the diagnostic chip holder 58. After that, the diagnostic chip collecting tray 52 and the diagnostic chip holder 58 are pushed toward the diagnostic apparatus 20 such that the diagnostic chip collecting tray 52 is situated in the diagnostic 410 chip collecting tray bay 56. After that, an analyzing step 114 can begin. When the diagnostic chip collecting tray 52 is situated in the diagnostic chip collecting tray bay 56, the diagnostic chip 26 is located underneath the optical sensor 48. Upon the receiving of the starting signal from the microprocessor, light beam from the illumination system 50 (e.g. a laser beam) is then directed onto the diagnostic chip 26 to generate at least one signal (if the mixed sample and reagent contains the analyte) detectable by the optical sensor 48. In one embodiment, the at least one signal includes fluorescence signal is generated when the diagnostic chip 26 radiated by the suitable light at suitable wavelength (e.g. 488 nm). The signal collected will be converted into digital data which will then be transferred to and analyzed in by the microprocessor of the control unit 28 to determine the presence of the analyte quantitatively or qualitatively. The result will be shown on the display unit 34 of the apparatus in relatively short period of time (fast) (e.g. in a range of 10-25 mins).

The control unit 28 further includes a non-transitory computer readable medium to store computer readable codes such that when it is executed by the microprocessor, it gives signals and control all the parts of the diagnostic apparatus 20 to perform and operate the steps as described above. The non-transitory computer readable medium may comprise any known type of data storage and/or transmission media, including magnetic media, optical media, random access memory (RAM), read-only memory (ROM), a data cache, a data object, etc. Moreover, memory may reside at a single physical location, comprising one or more types of data storage, or be distributed across a plurality of physical systems in various forms.

In one embodiment, the control unit 28 comprises of software modules which might be needed for system operation. The modules include operating system, application module, image processing module, microfluidic cartridge driver software module for controlling the flow of fluids in the microfluidic chip 24 as aforesaid and user interface software module. The operating system manages computer hardware resources and provides common services for all the computer software modules. The operating system can be Apple iOS, Android, Microsoft windows or Linux. The operating system is also integrated various communication protocols, be it wired or wireless, such local area network (LAN), USB, Wi-fi, Bluetooth, etc. The application module is a set of programs designed to carry out operations for the apparatus. It manages the data of the apparatus as well as job data, program data, client data, microfluidic cartridge data, pump setting, optical sensor setting, and the data collected from the optical inspection unit 32. The image processing module collects the data from the optical inspection unit 32. The image processing module selects areas of interest of the diagnostic chip 26 and control the acquiring of images there from. The image processing module also corrects the brightness and contrast of the images acquired. Upon receiving these images from the image processing module, the control unit 28 measures and compares the images of the diagnostic chip 26 according to the setting of the optical sensor 48. The image processing module then counts and calculates according to the set limits will send the analyzed results to the user interface software module. The microfluidic cartridge driver software module is designed to instruct the microfluidic cartridge driver unit 30 to control the current and the time of delivering such current to the microfluidic pump at the microfluidic chip 24. The higher the current and/or the longer the time for delivering such current, the more fluids can then be pumped from the reservoirs 80. The user interface software module is the interface that allows users to interact with the apparatus through graphical icons, visual indicators such as notations and commands. The user interface software module makes the apparatus very user-friendly to non-skilled persons by allowing the user to obtain, understand, add, edit and delete information easily without any special skills. It also allows user to feel that they have close connections with the optical inspection unit 32, with the help of interactivity of graphic, sound, as well as the delivery of notifications and commands given by the user interface software module.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

For example a power supply unit is needed to run the system but is not described in detail as it is clear to one skilled in the art that electrical power is needed for the operation of the apparatus. The unit includes at least one rechargeable battery pack, battery charger port, power switch, and power management electronic circuit. The conventional rechargeable battery pack can be made of lithium ion, lithium polymer or other high capacity battery. The rechargeable battery pack in the power supply unit can support a few hours of operation of the apparatus without public electrical supply, say in remote locations. The power supply unit is equipped with a battery protection circuitry which can protect the rechargeable battery pack against over charge, over current and over temperature so as to guarantee the safety of the apparatus and user. The power supply unit is also equipped with a battery connector to let the user replaces the fully discharged battery by a spare fully charged battery when there is an extended hours of use. The power management electronic circuit is used for converting the rechargeable battery pack voltage to different voltage as required by different system units. The power management electronic circuit is connected with the control unit 28, the rechargeable battery pack, the microfluidic cartridge driver unit 30 and the optical inspection module. The power management electronic circuit allows the initiation, termination and alteration of the voltage whenever it is needed to save the power consumption of the apparatus. These command signals are given by the control unit 28. Moreover, the battery charger provides Direct current (DC) to charge up the rechargeable battery pack in the system via the battery charger port at the back panel of the apparatus. The apparatus can operate even when the rechargeable battery pack is empty but when public electric supply is presented. The battery charger port can be detached when the rechargeable battery pack is charged Up.

The apparatus can further include at least one USB port or any other data communication means to allow the operation of common communication protocols of data transfer. The display unit is equipped in the apparatus for human interface. The display unit is a high resolution color display that can be either a liquid-crystal display (LCD), Organic Light-Emitting Diode (OLED) or other kind of display. The display unit can be incorporated with a touch screen panel; therefore, it can receive command from the touch of human fingers. The display unit is connected with the control unit 28. However, the way it displays, the content being displayed is made by the graphic user interface.

An exemplary microfluidic chip that can be used can be the microfluidic chip disclosed in German patent application numbers DE102010061910.8 and DE102010061909.4.

Figure 12:
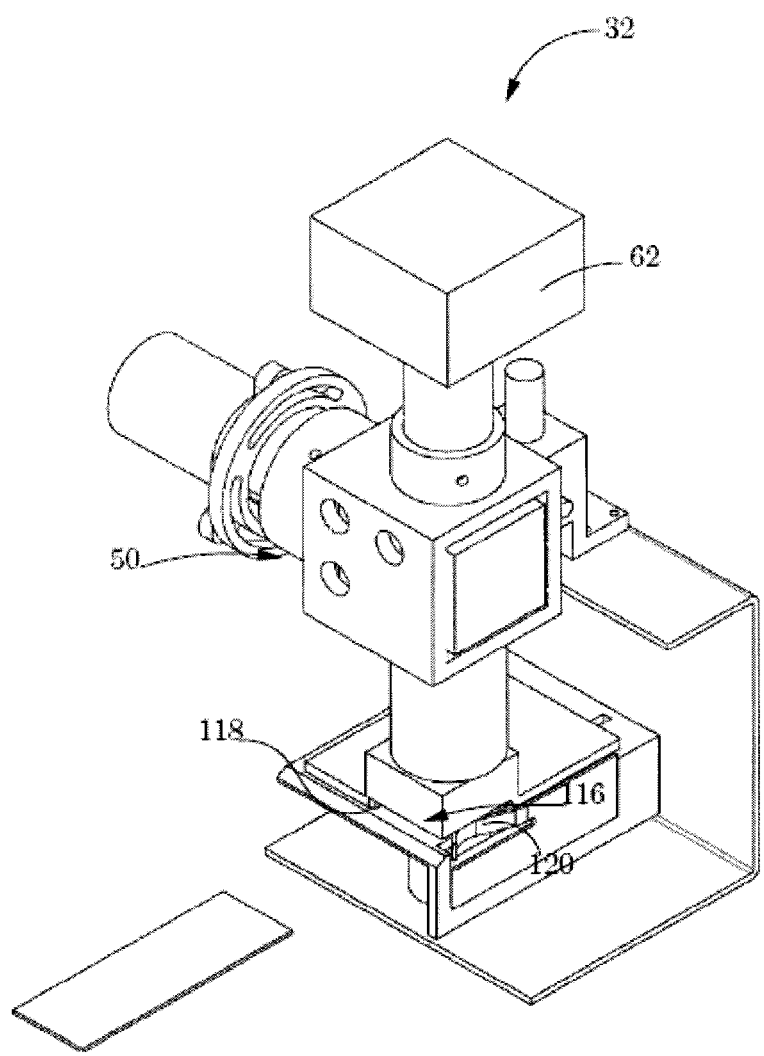
FIG. 12 is a schematic view of the optical inspection unit of the diagnostic system, according to an alternative embodiment of the present invention.

In one alternative embodiment, the diagnostic chip collecting tray 52 of the inspection unit 32 can be replaced by an analyzing slot 116 as shown in FIG. 12. The analyzing slot 116 comprises a diagnostic chip collecting slot 118 configured to receive the diagnostic chip 26 and allow it to slide into the optical inspection unit 32 of the diagnostic apparatus 20. The opening of the diagnostic chip collecting slot 118 has a size slightly bigger than the diagnostic chip 26 so that the diagnostic chip 26 can be slid into the optical inspection unit 32 at a designated orientation. The analyzing slot 116 is further configured to hold the diagnostic chip 26 at a predetermined position in the diagnostic chip collecting slot 118, wherein the predetermined position is beneath the optical sensor 48 of the camera 62 for the analysis. A slot hook 120 is also provided at the analyzing slot 116, wherein the slot hook 120 is configured to directly hold the diagnostic chip 26 at the predetermined position for the analysis and directly release the diagnostic chip 26 after that.

In yet another alternative embodiment, instead of using the at least one laser beam, at least one light beam can be used generate at least one signal for the analysis. The illumination system 50 in this alternative embodiment emits at least one light beam with at least one predetermined wavelength on the diagnostic chip 26. The illumination system 50 comprises a light-emitting diode (LED), at least one filter and at least one dichroicmirror.

In another embodiment, the illumination system 50 can have more than one diode laser or more than one LED.

In yet another embodiment, the camera 62 of the inspection unit 32 can be a digital high resolution camera 62, in which the sensor is selected from a group of Complementary metal-oxide-semiconductor (CMOS) sensor and Charge-coupled device (CCD) sensor. The megapixels of the image sensor of the digital high resolution camera 62 is in a range of 1.0 Megapixels to 30 Megapixels.

In yet other embodiment, the diagnostic apparatus 20 can include multiple microfluidic cartridge driver units 30 and multiple optical inspection units 32 so that the multiple analyses/diagnoses can be run at the same time.

What is claimed is:

1. An apparatus for detecting at least one analyte from a sample, the apparatus comprising:
   (a) a microfluidic cartridge comprising a diagnostic chip for interacting or reacting with said analyte and a microfluidic chip attached thereto, wherein the microfluidic chip comprises a plurality of reservoirs for holding one or more samples and reagents, and a plurality of hydro gel micro-pumps, wherein each one of said hydro gel micro-pumps abuts a corresponding one of said reservoirs;
   (b) a microfluidic cartridge driver unit comprising:
      (1) a cartridge chamber configured to receive the microfluidic cartridge; and
      (2) at least one electrical connector configured to connect with said microfluidic cartridge and provide electrical current and control signals to operate each of said hydro gel micro-pumps;
   (c) an optical inspection unit configured to detect at least one signal generated from said diagnostic chip, said unit comprising:
      (1) a collecting tray configured to receive at least said diagnostic chip of said microfluidic cartridge;
      (2) an illumination system configured to deliver light directly to said diagnostic chip; and
      (3) an optical sensor configured to detect signal generated from said diagnostic chip;
   (d) a control unit configured to control the quantitative and qualitative analysis, interfacing, and storage of signal obtained from said optical inspection unit; and control and monitor the operation of said apparatus.

2. The apparatus of claim 1, wherein said optical sensor comprises at least one objective integrated to a high resolution camera.

3. The apparatus of claim 2, wherein said high resolution camera is a digital camera.

4. The apparatus of claim 3, wherein said illumination system comprises at least one diode laser with a wavelength of 400-500 nm.

5. The apparatus of claim 4, wherein said analyte is influenza virus antigen and said wavelength of said diode laser is 488 nm.

6. The apparatus of claim 1, wherein said apparatus comprises a power supply comprising a built-in rechargeable battery.

7. The apparatus of claim 1, wherein the microfluidic chip is further configured to drive said sample and said reagent from said plurality of reservoirs to said diagnostic chip; and wherein said diagnostic chip is pre-coated with an array of detection spots, which is configured to interact or react with said analyte for generating at least one signal at a predetermined condition.

8. The apparatus of claim 1, wherein the microfluidic chip comprises an electrical connecting interface and at least one micro fluidic channel.

9. The apparatus of claim 8, wherein the control unit comprises a microprocessor configured to execute computer readable codes for the following steps:
   (1) providing electrical current and control signals through the electrical connector to the electrical connecting interface of the microfluidic cartridge to instruct said microfluidic cartridge driver unit to control the expansion and contraction of each of said hydro gel micro-pumps of the microfluidic cartridge, such that each of said hydro gel micro-pumps drives said sample and said reagent from a corresponding reservoir in the microfluidic chip to the diagnostic chip through the microfluidic channels whereby said sample is mixed with said reagent in said microfluidic cartridge at a predetermined time, speed and sequence;
   (2) optionally providing electrical current and control signals through the electrical connector to the electrical connecting interface of the microfluidic cartridge to spread a secondary auxiliary reagent located at one of the reservoirs by flowing through the microfluidic channels of the microfluidic chip to the diagnostic chip for attaching a secondary molecule for facilitating the detection of reacted or interacted analyte;
   (3) providing a starting signal to the illumination system to direct a light beam onto the diagnostic chip to generate at least one signal detectable by the optical sensor; and
   (4) analyzing the signal detected by the optical sensor to determine the presence of the analyte quantitatively or qualitatively.

10. An apparatus for detecting at least one analyte from a sample, the apparatus comprising:
   (a) a microfluidic cartridge comprising a diagnostic chip for interacting or reacting with said analyte and a microfluidic chip attached thereto, wherein the microfluidic chip comprises a plurality of reservoirs for holding one or more samples and reagents, and a plurality of hydro gel micro-pumps, wherein each one of said hydro gel micro- pumps is located adjacent to, and in physical contact with, a corresponding one of said reservoirs whereby expansion and contraction of each one of said hydro gel micro-pumps causes fluid to move in each corresponding one of said reservoirs;
   (b) a microfluidic cartridge driver unit comprising:
      (1) a cartridge chamber configured to receive the microfluidic cartridge; and
      (2) at least one electrical connector configured to connect with said microfluidic cartridge and provide electrical current and control signals to operate each of said hydro gel micro-pumps;
   (c) an optical inspection unit configured to detect at least one signal generated from said diagnostic chip, said unit comprising:
      (1) a collecting tray configured to receive at least said diagnostic chip of said microfluidic cartridge;
      (2) an illumination system configured to deliver light directly to said diagnostic chip; and
      (3) an optical sensor configured to detect signal generated from said diagnostic chip;
   (d) a control unit configured to control the quantitative and qualitative analysis, interfacing, and storage of signal obtained from said optical inspection unit; and control and monitor the operation of said apparatus.

* * * * *